(12) United States Patent
Yurgil et al.

(10) Patent No.: US 6,436,712 B1
(45) Date of Patent: Aug. 20, 2002

(54) APPARATUS AND METHOD FOR MONITORING INTERNAL COMBUSTION EXHAUST

(75) Inventors: James R. Yurgil, Livonia; Guy E. LaFalce, Romeo, both of MI (US)

(73) Assignee: General Motors Corporation, Detroit, MI (US)

( * ) Notice: Subject to any disclaimer, the term of this patent is extended or adjusted under 35 U.S.C. 154(b) by 0 days.

(21) Appl. No.: 09/862,765

(22) Filed: May 21, 2001

(51) Int. Cl.[7] .............................................. G01N 35/08
(52) U.S. Cl. ........................... 436/55; 422/98; 422/62; 422/83; 422/108; 422/117; 422/119; 436/68; 436/134; 74/866; 123/396
(58) Field of Search .............................. 422/98, 62, 83, 422/108, 117, 119; 436/55, 68, 134; 74/866; 123/396

(56) References Cited

U.S. PATENT DOCUMENTS

| | | | | |
|---|---|---|---|---|
| 3,471,391 A | * | 10/1969 | Peters et al. | 204/277 |
| 3,474,022 A | * | 10/1969 | Culpepper et al. | 204/431 |
| 3,479,257 A | * | 11/1969 | Shaver | 204/274 |
| 3,493,484 A | * | 2/1970 | Berg et al. | 204/407 |
| 3,830,630 A | * | 8/1974 | Kiefer et al. | 422/84 |
| 4,324,556 A | * | 4/1982 | Robertson et al. | 356/40 |
| 4,665,385 A | * | 5/1987 | Henderson | 250/497.1 |
| 5,526,280 A | * | 6/1996 | Consadori et al. | 340/632 |

* cited by examiner

*Primary Examiner*—Jill Warden
*Assistant Examiner*—Jennine Brown
(74) *Attorney, Agent, or Firm*—Christopher DeVries

(57) ABSTRACT

A method and apparatus according to the present invention monitors an emission gas, such as a carbon monoxide gas, from an emission source, such as a carbon monoxide source, by periodically sensing a concentration level of emission gas, such as carbon monoxide, in ambient air and generating a signal corresponding to the sensed concentration level of the emission gas. In response to the signal, a percent blood concentration value of the emission gas is determined. The calculated blood concentration value is compared to a threshold value, and if greater than the threshold value, the source of emission gas, such as carbon monoxide gas, is disabled. The blood concentration value can be determined on a predetermined time interval, and at least in part, can be based on a prior blood concentration value in combination with a current blood concentration value.

22 Claims, 3 Drawing Sheets

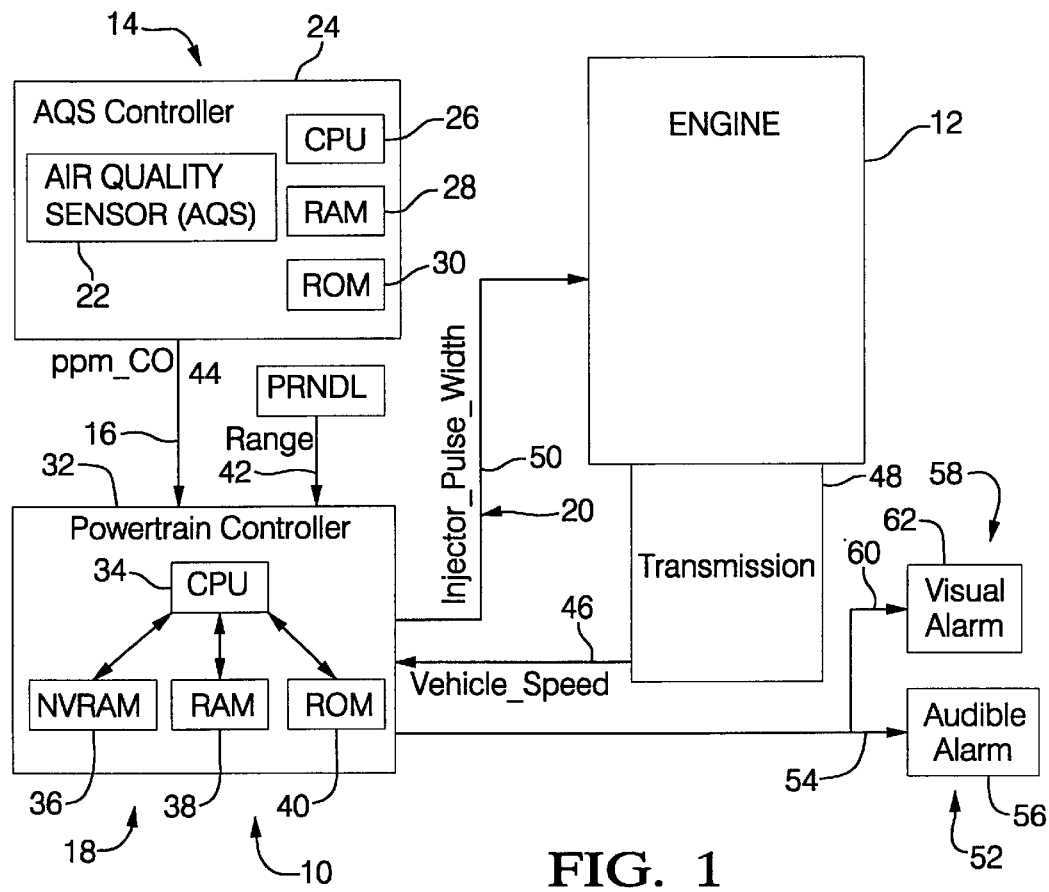
FIG. 1
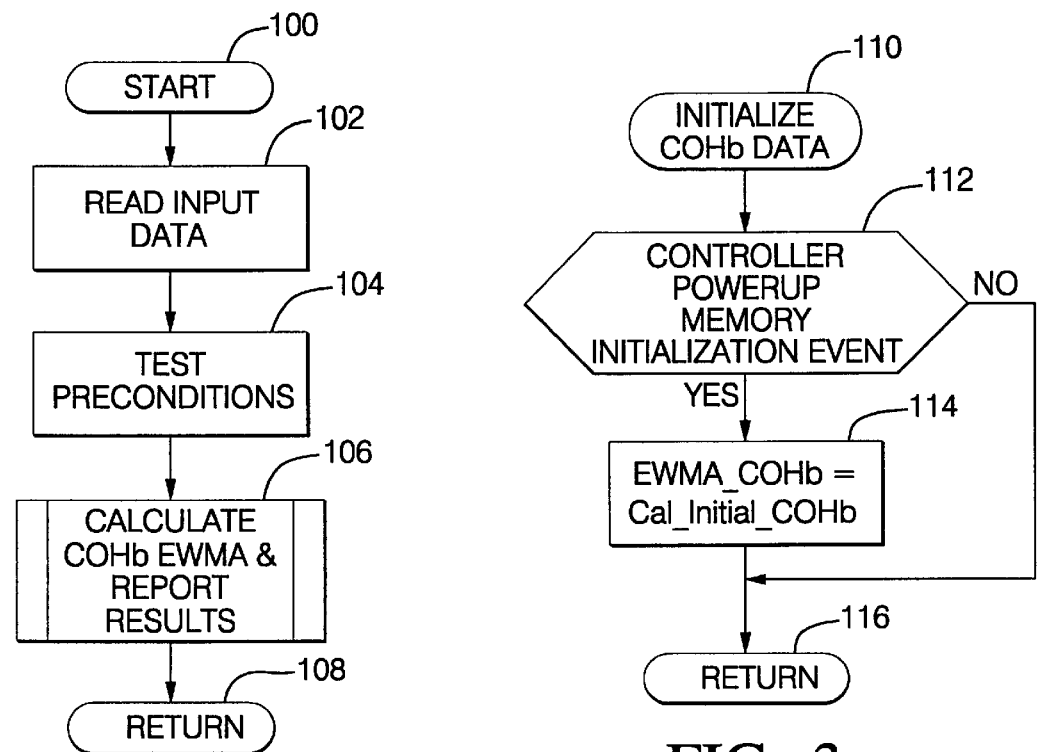
FIG. 2
FIG. 3

APPARATUS AND METHOD FOR MONITORING INTERNAL COMBUSTION EXHAUST

FIELD OF THE INVENTION

The present invention relates to an apparatus and method for monitoring an emission gas, such as carbon monoxide gas, from an emission source, such as a carbon monoxide source.

BACKGROUND OF THE INVENTION

Air quality sensors have been used to detect rapid changes in $NO_x$, CO, and hydrocarbon concentration using a single or dual $SnO_2$ based sensing element. The information is typically used to control the recirculation door of a conventional automobile heating, ventilating and air conditioning system.

SUMMARY OF THE INVENTION

It is desirable in the present invention to use air quality sensors to extract or determine absolute concentration level information that has not been previously available. The present invention includes an apparatus and a method for monitoring emission gas, using air quality sensors, for detecting the presence of an emission gas, such as carbon monoxide, and then determining if the detected concentration levels warrant disablement of further operation by the source of the emissions, such as an internal combustion engine. The present invention is desirable to enable stationary, unattended electrical power generation equipment to be incorporated into a motor vehicle. It is desirable to add electrical power take off devices on future model year automobiles. The present invention measures the quality of the air surrounding the vehicle and can assess if disablement of the engine is appropriate based on the measurement.

An apparatus according to the present invention monitors emission gases, such as carbon monoxide gas, from an emission source by periodically sensing a concentration level of emission gas, such as carbon monoxide, in ambient air and by generating a signal corresponding to the sensed concentration levels. In response to the signal, a determination is made regarding a percent blood concentration value, such as carboxyhemoglobin blood concentration value. A source of emission gas, such as carbon monoxide gas, is disabled when the calculated blood concentration value is greater than a threshold value.

The apparatus and method according to the present invention can include an air quality sensor with a first central processing unit for measuring a concentration level of carbon monoxide in ambient air, and a second central processing unit for calculating a percent carboxyhemoglobin blood concentration value based on the measured concentration level and sending a shut off signal if the blood concentration value is greater than a threshold value, and an engine control for disabling the carbon monoxide source in response to the shut off signal.

Other objects, advantages and applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein:

FIG. 1 is a simplified schematic diagram of an apparatus for monitoring internal combustion exhaust gases during unattended operation according to the present invention;

FIG. 2 is a simplified flow diagram for a carboxyhemoglobin exponentially weighted moving average algorithm based program;

FIG. 3 is a simplified flow diagram for initializing a percent carboxyhemoglobin estimator according to the present invention;

DESCRIPTION OF THE PREFERRED EMBODIMENT

Figure 4:
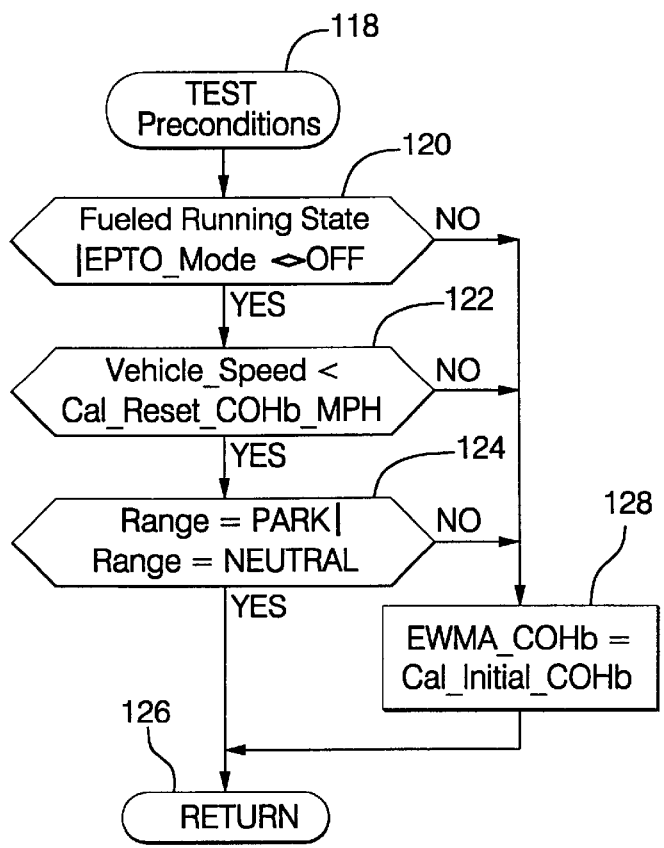
FIG. 4 is a simplified flow diagram for determining if preconditions for testing have been met according to the present invention.

Referring now to FIG. 1, an apparatus 10 is illustrated for monitoring emission gases, such as carbon monoxide gas, from an emission source, by way of example and not limitation, such as engine 12. The apparatus 10 can include means 14 for periodically sensing a concentration level of emission gas, such as carbon monoxide gas, in ambient air, and for generating a signal 16 corresponding to the sensed concentration level of the gas. Means 18 is responsive to the signal 16 for determining a percent blood concentration value of the emission gas, such as carboxyhemoglobin blood concentration value. The apparatus 10 can include means 20 for disabling a source 12 of emission gas, such as carbon monoxide gas, when the blood concentration value is greater than a threshold value.

In the preferred configuration, means 14 periodically senses a concentration level of carbon monoxide in ambient air and generates a signal corresponding to the carbon monoxide concentration level. Periodic sensing means 14 can include an air quality sensor (AQS) 22 and controller 24. The air quality controller 24 can include a first central processing unit (CPU) 26, random access memory (RAM) 28, and read only memory (ROM) 30. In the preferred configuration, the sensor and controller are integrated into a single unit that responds to the presence of carbon monoxide, and provides a useable output signal in response to the presence of carbon monoxide. The present invention monitors emission gases, using the air quality sensor, for the presence of carbon monoxide, and then determines if the detected concentration levels warrant disablement of further operation of the source of the emissions.

Means 18 determines a percent carboxyhemoglobin blood concentration value responsive to the signal corresponding to the sensed carbon monoxide concentration level. Determining means 18 can include a controller 32, such as a power train controller. The controller 32 can include a second central processing unit (CPU) 34, non-volatile random access memory (NVRAM) 36, random access memory (RAM) 38, and read only memory (ROM) 40. The controller 32 can receive a signal 42 corresponding to a gear selected by the gear shift selector 44. This allows the controller 32 to determine if the vehicle gear selected is "park" or "neutral" as a precondition for testing. The gear shift selector 44 can provide the signal 42 to the controller 32. The controller 32 can also receive a signal 46 to determine as a precondition for testing if the vehicle speed is approximately equal to zero. In FIG. 1, the velocity signal 46 is generated by the transmission 48 connected to the engine 12.

Means 20 disables a source 12 of carbon monoxide gas when the blood concentration value is greater than a threshold value. Disabling means 20 can include an injector pulse width signal 50 capable of stopping flow of fuel to the source 12 of carbon monoxide gas in response to a percent carboxyhemoglobin blood concentration value greater than a predetermined threshold value. The controller 32 can generate the injector pulse width signal 50. Preferably, the blood concentration value is determined on a predetermined time interval, and at least in part, is based on a prior blood concentration value in combination with a current blood concentration value.

The determining means 18, or controller 32, can compare the blood concentration value to a plurality of threshold values. One of the plurality of threshold values can correspond to a first alarm value. The apparatus 10 according to the present invention can include means 52 for producing an audible alarm when the blood concentration value is greater than the first alarm value. Producing means 52 can include an audible alarm signal 54 generated by the controller 32 for receipt by an audible alarm 56.

One of the plurality of threshold values can include a second alarm value. Means 58 can be provided for producing a visual alarm when the blood concentration value is greater than the second alarm value. The producing means 58 can include a visual alarm signal 60 generated by the controller 32 to be received by a visual alarm 62.

The present invention provides a method for determining the estimated percent carboxyhemoglobin (COHb) in blood from sensed concentrations of carbon monoxide. The method according to the present invention provides for initializing the percent carboxyhemoglobin estimator prior to enabling the operation of the estimator. One or more alarm thresholds are used to determine if an audible and/or visual signal should be actuated to indicate a monitored condition that has caused blood carboxyhemoglobin levels to exceed the permissible predetermined levels, and/or for disabling further operation of the source of carbon monoxide gas, such as an internal combustion engine powering a generator. The method steps according to the present invention can be performed by one or both of the controllers 24, 32.

The carboxyhemoglobin estimator according to the present invention is programmed to operate in accordance with a carbon monoxide alarm industry accepted relationship between the percent carboxyhemoglobin in blood as a function of carbon monoxide concentration (parts per million carbon monoxide (PPM CO)) and time as given by the following equation:

$$\% \text{ COHb}_t = \% \text{ COHb}_0[e^{-(t/2398 \cdot B)}] + 218[1 - e^{-(t/2398 \cdot B)}][0.0003 + (\text{ppm CO}/1316)]$$

where: $\% \text{ COHb}_t$ is the percent of carboxyhemoglobin at time t; $\% \text{ COHb}_0$ is the percentage of carboxyhemoglobin in blood at time 0; t is the time in minutes; B is 0.0404 corresponding to a heavy work effort; and ppm CO is the carbon monoxide concentration at time t.

A discreet time sampled data form of this relationship suitable for controller implementation was derived and is of the form of a classic, discreet time first-order lag filter or exponentially weighted moving average (EWMA) equation as follows:

$$\% \text{ COHb}(n) = \% \text{ COHb}(n-1) + \lambda^*[218^*(0.0003 + \text{ppm\_CO}/1316) - \% \text{ COHb}(n-1)]$$

where: $\% \text{ COHb}(n)$ is the new estimate of the percentage of COHb in blood; $\% \text{ COHb}(n-1)$ is the previous estimate of the percentage of COHb in blood; ppm_CO is the CO concentration at time nT; T is the sampling period in minutes; $\lambda$ is the filter coefficient or weighting factor where $\lambda = (1 - e^{-(T/2398 \cdot B)})$, $0 \leq \lambda \leq 1$ for this relationship to be valid; and $218^*(0.0003 + \text{ppm\_CO}/1316)$ is the exponentially weighted moving average (EWMA) process variable and represents the estimated long term percent COHb in blood should the ambient CO concentration persist.

FIGS. 2 through 5 illustrate the preferred logic flow diagrams associated with initializing and enabling the percent carboxyhemoglobin estimator according to the present invention. In general, initialization of the carboxyhemoglobin initial value occurs at controller power up as well as at vehicle speed greater than a non-zero threshold. The preconditions to enable the test include vehicle speed approximately equal to zero and gear selected being equal to park or neutral. These precondition criteria are used to identify potential enclosed operating modes of the carbon monoxide source. Calculation of the percentage of carboxyhemoglobin occurs once for each time interval, T, whenever the enable criteria is met. The alarm threshold is a constant value above which an alarm is activated, and corrective action will occur. Typical acceptable alarm threshold ranges are 5% to 10% inclusive of carboxyhemoglobin concentration. Once an alarm is activated, the carbon monoxide source, such as an engine, will be halted. Preferably, further injection of fuel is disabled to halt further operation of the engine. The disabling of fuel injection can be accomplished through standard combustion engine controls, remote start controls, or auto-start capabilities associated with the particular engine. Preferably, a manual key initiated start is required to force a restart of the engine. Disablement will reoccur if a calibrated amount of time passes without vehicle movement and a transition out of a park or neutral gear state does not occur after restarting the engine.

Referring now to FIG. 2, a method for monitoring an emission gas from an emission source, such as carbon monoxide gas from a carbon monoxide source, is illustrated. The control program begins at step 100 where the program starts and continues to step 102 where the input data is read in order to initialize the system. After initialization, the program continues to step 104 where it is determined if the test preconditions exist. If the test preconditions exist, the program continues onto step 106 where the carboxyhemoglobin exponentially weighted moving average is calculated and the results are reported. After reporting the results in step 106, the program continues to step 108 where the program returns to the beginning.

Referring now to FIG. 3, the input data read portion of the program is illustrated in more detail beginning with step 110 where the carboxyhemoglobin data is initialized. After the initialization in step 110, the program continues to query 112 where it is determined if a controller power up memory initialization event has occurred. If the answer to query 112 is yes, the program continues to step 114 where the exponentially weighted moving average (EWMA) carboxyhemoglobin (COHb) is set initially equal to a predetermined initial carboxyhemoglobin value. After completing step 114, or if the answer to query 112 is no, the program continues to step 116 where the program returns to the main program.

Referring now to FIG. 4, the test preconditions of step 104 are shown in greater detail. The precondition testing routine begins with step 118. The program continues to query 120 where it is determined if a fueled running state exists, or if the electric power take off (EPTO) does not equal off. If the answer to query 120 is yes, the program continues to query 122 where the program determines if the vehicle speed is less then a predetermined reset carboxyhemoglobin mile-per-hour value. If the answer to query 122 is yes, the program continues to query 124 where the program determines if the gear selector is in a range equal to park, or in a range equal to neutral. If the answer to query 124 is yes, the program continues to step 126 where the program returns to the main program. If the answer to query 120 is no, or if the answer to query 122 is no, or if the answer to 124 is no, the program branches to step 128 where the exponentially weighted moving average carboxyhemoglobin value is set equal to a predetermined initial carboxyhemoglobin value prior to continuing to step 126 where the program returns to the main program.

Figure 5:
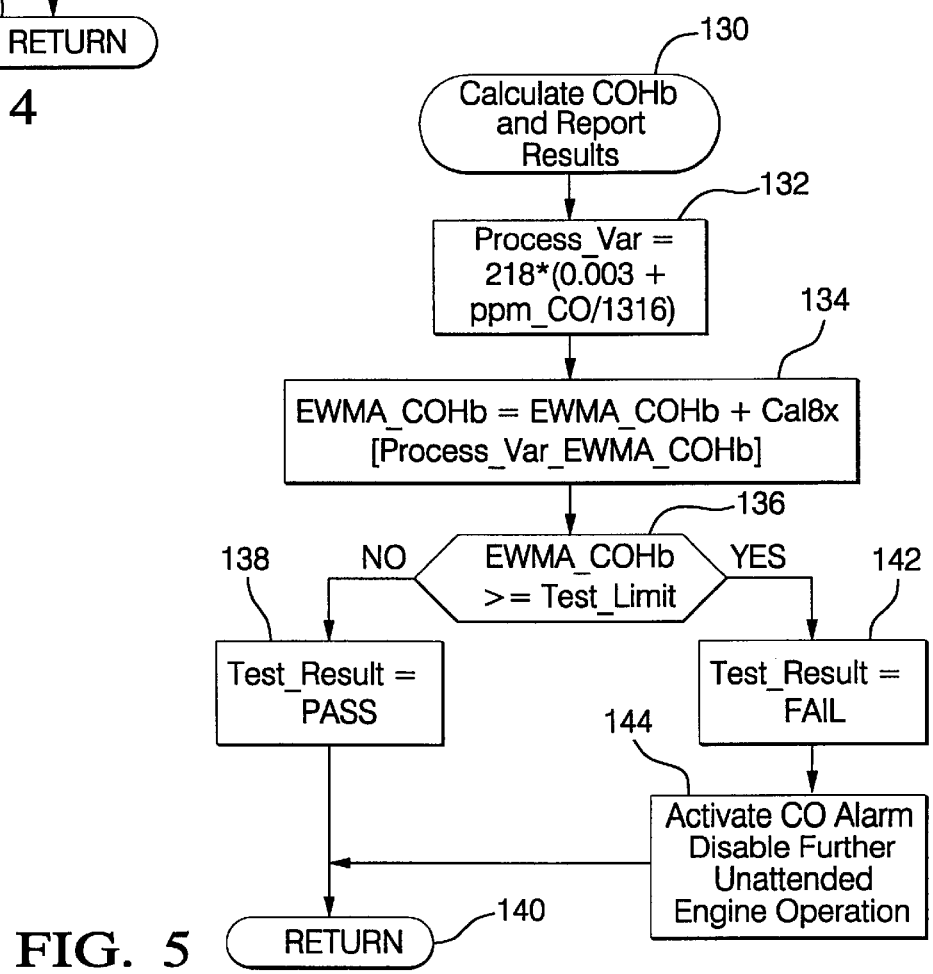
FIG. 5 is a simplified flow diagram for calculating carboxyhemoglobin concentration levels and reporting results according to the present invention.

Referring now to FIG. 5, the calculation step 106 is shown in greater detail. The calculated carboxyhemoglobin and report results subroutine begins at step 130. The program continues to step 132 where a process variable is set equal to a value corresponding to the following equation:

Process_Var=218*(0.0003+ppm_CO/1316)

After setting the process variable in step 132, the program continues to step 134 where the exponentially weighted moving average carboxyhemoglobin value is set according to the following equation:

EWMA_COHb=EWMA_COHb+Cal8×[Process_Var—EWMA_COHb)]

After the exponentially weighted moving average carboxyhemoglobin value has been set in step 134, the program continues to query 136 where it is determined if the exponentially weighted moving average carboxyhemoglobin value is greater than or equal to a predetermined test level or threshold value. If the answer to query 136 is no, the program continues to step 138 where the test result is reported as a "pass". After setting the test result equal to "pass" in step 138, the program continues to step 140 where the program returns to the main program. If the answer to query 136 is yes, the program branches to step 142 where the test result is reported as a "fail". After the test result is reported as a "fail" in step 142, the program continues to step 144 where a carbon monoxide alarm is activated and further unattended engine operation is disabled. After the alarm is activated and the engine is disabled in step 144, the program continues to step 140 where the program returns to the main program.

Figure 6:
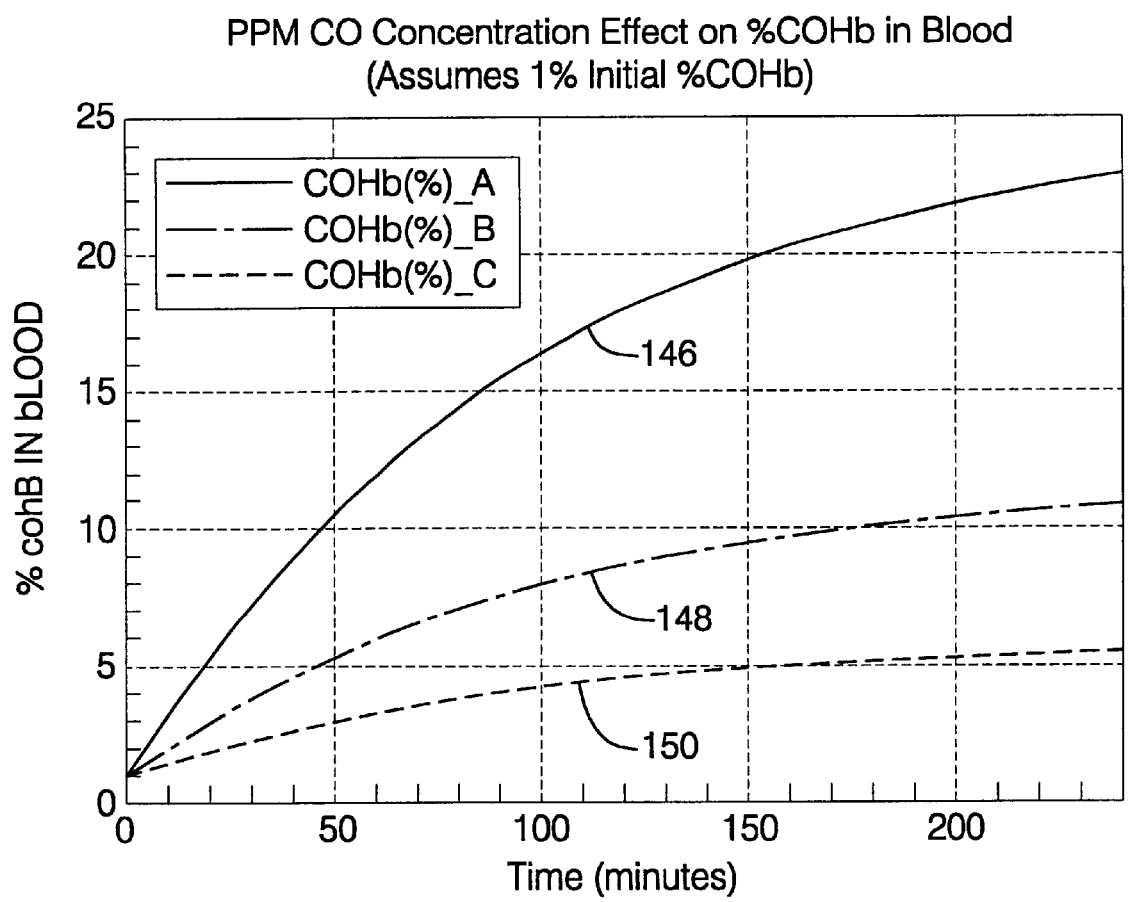
FIG. 6 is a graph illustrating parts per million carbon monoxide concentration effect on percent carboxyhemoglobin in blood assuming a 1% initial percent carboxyhemoglobin concentration where the vertical axis illustrates percent carboxyhemoglobin in blood and the horizontal axis illustrates time in minutes.

Referring now to FIG. 6, a graph is provided illustrating percent carboxyhemoglobin in blood along the y axis versus time in minutes along the x axis with the parts per million (ppm) carbon monoxide (CO) concentration effect on percent carboxyhemoglobin (COHb) in blood assuming a 1% initial percent carboxyhemoglobin value. Three lines 146, 148, 150 are illustrated on the graph depicting various levels of carbon monoxide concentrations over time and the impact that the level has on the percent carbon monoxide hemoglobin in blood.

The method according to the present invention periodically senses a concentration level of carbon monoxide and ambient air and sends a signal corresponding to the carbon monoxide concentration level. The method then determines in response to the signal a percent carboxyhemoglobin blood concentration value. The method then determines if the blood concentration value is greater than a threshold value, and if so, disables the source of carbon monoxide gas. Preferably, the blood concentration value is determined on a predetermined time interval, and at least in part, is based on a prior blood concentration value in combination with a current blood concentration value.

The determining step according to the present invention can include the steps of comparing the blood concentration value to a plurality of threshold values. One of the plurality of threshold values can correspond to a first alarm value, where the blood concentration value is compared to the first alarm value, and an audible alarm is activated when the blood concentration value is greater than the first alarm value. The plurality of threshold values can also correspond to a second alarm value where the blood concentration value is compared to the second alarm value, and a visual alarm is activated when the blood concentration value is greater than the second alarm value.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. An apparatus for monitoring emission gas from an emission source comprising:
    means for periodically sensing a concentration level of emission gas in ambient air and for generating a signal corresponding to the sensed concentration level emission gas;
    means, responsive to the signal, for determining a percent blood concentration value of emission gas; and
    means for disabling a source of emission gas when the blood concentration value is greater than a threshold value.

2. The apparatus of claim 1, wherein the blood concentration value is determined on a predetermined interval and, at least in part, based on a prior blood concentration value in combination with a current blood concentration value.

3. The apparatus of claim 1, wherein said determining means compares the blood concentration value to a plurality of threshold values.

4. The apparatus of claim 3, wherein one of the plurality of threshold values is a first alarm value.

5. The apparatus of claim 4 further comprising means for producing an audible alarm when the blood concentration value is greater than the first alarm value.

6. The apparatus of claim 3, wherein one of the plurality of threshold values is a second alarm value.

7. The apparatus of claim 6 further comprising means for producing a visual alarm when the blood concentration value is greater than the second alarm value.

8. The apparatus of claim 1 wherein the emission gas is carbon monoxide.

9. A method for monitoring emission gas from an emission source comprising the steps of:
    periodically sensing a concentration level of emission gas in ambient air and sending a signal corresponding to the concentration level of emission gas;
    determining, in response to the signal, a percent blood concentration value of emission gas; and
    disabling a source of emission gas when the blood concentration value is greater than a threshold value.

10. The method of claim 9, wherein the blood concentration value is determined on a predetermined interval and, at least in part, based on a prior blood concentration value in combination with a current blood concentration value.

11. The method of claim 9, wherein the determining step further comprises the step of comparing the blood concentration value to a plurality of threshold values.

12. The method according to claim 11, wherein one of the plurality of threshold values corresponds to a first alarm value.

13. The method of claim 12 further comprising the steps of:

comparing the blood concentration value to the first alarm value; and activating an audible alarm when the blood concentration value is greater than the first alarm value.

14. The method of claim 11, wherein one of said a plurality of threshold values corresponds to a second alarm value.

15. The method of claim 14 further comprising the steps of:

comparing the blood concentration value to the second alarm value; and activating a visual alarm when the blood concentration value is greater than the second alarm value.

16. The method of claim 9 wherein the emission gas is carbon monoxide.

17. An apparatus for monitoring emission gas from an emission source comprising:

an air quality sensor for measuring a concentration level of carbon monoxide in ambient air;

a first central processing unit for calculating a percent carboxyhemoglobin blood concentration value based on the measured concentration level;

a second central processing unit for sending a shutoff signal if the blood concentration value is greater than a threshold value; and an engine control for disabling the carbon monoxide source in response to the shutoff signal.

18. The apparatus of claim 17, wherein the second central processing unit compares the blood concentration value to a plurality of threshold values.

19. The apparatus of claim 18, wherein one of the plurality of threshold values is a first alarm value.

20. The apparatus of claim 19 further comprising an audible alarm, and wherein the second processing unit is further capable of sending an audible alarm signal to the audible alarm when the blood concentration is greater than the first alarm value.

21. The apparatus of claim 18 wherein one of the plurality of values is a second alarm value.

22. The apparatus of claim 21 further comprising a visual alarm, and wherein said second processing unit is further capable of sending a visual alarm signal to the visual alarm when the blood concentration is greater than the second alarm value.

* * * * *